(12) United States Patent
Gelotte et al.

(10) Patent No.: US 9,668,993 B2
(45) Date of Patent: Jun. 6, 2017

(54) NON-STEROIDAL ANTI-INFLAMMATORY DRUG DOSING REGIMEN

(75) Inventors: Cathy K. Gelotte, Blue Bell, PA (US); Douglas R. Hough, Morrisville, PA (US); Gerard P. McNally, Berwyn, PA (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 1051 days.

(21) Appl. No.: 12/796,889

(22) Filed: Jun. 9, 2010

(65) Prior Publication Data

US 2010/0249237 A1     Sep. 30, 2010

Related U.S. Application Data

(62) Division of application No. 10/393,755, filed on Mar. 21, 2003, now abandoned.

(51) Int. Cl.
| | |
|---|---|
| A61K 31/192 | (2006.01) |
| A61K 31/00 | (2006.01) |
| A61K 33/24 | (2006.01) |
| A61K 9/16 | (2006.01) |
| A61K 9/50 | (2006.01) |

(52) U.S. Cl.
CPC .......... *A61K 31/192* (2013.01); *A61K 9/5084* (2013.01); *A61K 31/00* (2013.01); *A61K 33/24* (2013.01); *A61K 9/1652* (2013.01); *A61K 9/5047* (2013.01)

(58) Field of Classification Search
None
See application file for complete search history.

(56) References Cited

U.S. PATENT DOCUMENTS

| | | | |
|---|---|---|---|
| 2,998,450 | A | 8/1961 | Wilbert et al. |
| 3,485,719 | A | 12/1969 | Rogovin |
| 4,221,778 | A | 9/1980 | Raghunathan |
| 4,279,926 | A | 7/1981 | Bruzzese et al. |
| 4,752,580 | A | 6/1988 | Downs |
| 4,762,709 | A | 8/1988 | Sheumaker |
| 4,788,220 | A | 11/1988 | Mody et al. |
| 4,847,077 | A | 7/1989 | Raghunathan |
| 4,859,461 | A | 8/1989 | Chow et al. |
| 4,873,231 | A | 10/1989 | Smith |
| 4,906,478 | A | 3/1990 | Valentine et al. |
| 4,940,588 | A | 7/1990 | Sparks et al. |
| 4,975,465 | A | 12/1990 | Motola et al. |
| 4,980,170 | A | 12/1990 | Schneider et al. |
| 5,183,829 | A | 2/1993 | Caldwell |
| 5,275,822 | A | 1/1994 | Valentine et al. |
| 5,374,659 | A | 12/1994 | Gowan, Jr. |
| 5,409,907 | A | 4/1995 | Blase et al. |
| 5,424,075 | A | 6/1995 | Daher et al. |
| 5,510,385 | A | 4/1996 | Stroppolo et al. |
| 5,527,545 | A | 6/1996 | Santus et al. |
| 5,621,005 | A | 4/1997 | Gowan, Jr. |
| 5,759,579 | A | 6/1998 | Singh et al. |
| 5,773,031 | A | 6/1998 | Shah et al. |
| 6,001,392 | A | 12/1999 | Wen et al. |
| 6,103,260 | A | 8/2000 | Luber et al. |
| 6,126,967 | A | 10/2000 | Clemente et al. |
| 6,126,969 | A | 10/2000 | Shah et al. |
| 6,197,347 | B1 | 3/2001 | Jan et al. |
| 6,254,891 | B1 | 7/2001 | Anaebonam et al. |
| 6,607,751 | B1 | 8/2003 | Odidi et al. |
| 2002/0031552 | A1 | 3/2002 | McTeigue et al. |
| 2004/0131671 | A1 | 7/2004 | Zhang et al. |
| 2004/0202716 | A1 | 10/2004 | Chan et al. |
| 2004/0242640 | A1 | 12/2004 | Desai et al. |

FOREIGN PATENT DOCUMENTS

| | | |
|---|---|---|
| CN | 1132070 A | 10/1996 |
| CN | 1356102 A | 7/2001 |
| CN | 1277550 A | 2/2011 |
| EP | 0717992 A2 | 6/1996 |
| WO | WO 96/01628 A1 | 1/1996 |
| WO | WO 94/41617 A | 12/1996 |
| WO | WO 96/41617 A | 12/1996 |
| WO | WO 97/41839 A1 | 11/1997 |
| WO | WO 98/41617 | 9/1998 |
| WO | WO 99/12524 A1 | 3/1999 |
| WO | WO 00/23055 | 4/2000 |
| WO | WO 0119350 A1 | 3/2001 |
| WO | WO 01/52815 | 7/2001 |

OTHER PUBLICATIONS

Roberts LJ, Morrow JD, Chapter 27 Analgesic-Antipyretic and Antiinflammatory Agents and Drugs Employed in the Treatment of Gout, "Goodman & Gilman's The Pharmacological Basis of Therapeutics, 10th ed." Hardman JG, Limbird LE, and Gilman AG, Eds., McGraw-Hill, 2001, 687-731 (pp. 687, 704, and 711 provided).*
XP-002146703(Cited solely for the figure illustrated).
USP 23 (1995) pp. 786.
USP 24, 2000 Version, 19-20 and 856-857 (1999).
Ameer, B. et al., "Acetaminophen", Annals of Internal Med. 87 (1977), pp. 202-209.
Kurumaddall, K.R. et al., "Preparation and evaluation of sustained release ibuprofen beads," Drug Development and Industrial Pharmacy, 20(17), (1994) pp. 2659-2669.
Lieberman, Herbert A. et al., "Pharmaceutical Dosage Forms: Tablets, Pan Coating of Tablets and Granules", vol. 3, (1982) pp. 73-117.
Lieberman, Herbert A. et al., "Pharmaceutical Dosage Forms: Tablets, Particle-Coating Methods", vol. 3, (1982) pp. 119-148.
Lieberman, Herbert A. et al., "Pharmaceutical Dosage Forms: Tablets, Sustained Drug Release from Tablets and Particles Through Coating", vol. 3, (1982) pp. 149-221.

(Continued)

*Primary Examiner* — Craig Ricci
(74) *Attorney, Agent, or Firm* — Victor Tsu

(57) ABSTRACT

A method of administering non-steroidal-anti-inflammatory drugs, in particular propionic acid derivatives such as ibuprofen, or acetaminophen is provided. This method provides improved therapeutic effect, in particular pain relief, over extended time periods.

23 Claims, 3 Drawing Sheets

(56) References Cited

OTHER PUBLICATIONS

Setty, Chitrali et al., "Development and in vito evaluation of multiparticulate sustained release formulation of diltizem hydrochloride using ethylcellulose and cellulose acetate phthalate," Indian Drugs 35(4) Apr. 1998, pp. 195-199.

Walter, K., et al., "Pharmacokinetics of ibuprofen following a single administration of a suspension containing enteric coated microcapsules." Arzneim-Forsch/ Drug Res. 45 (II), Nr. 8 (1995), pp. 886-890.

Bellamy N. (Reprint) et al: "A comparative-analysis of 2 Dosing Strategies of Flurbiprofen in Rheumatoid-Arthritis—An Application of Sequential Trial Design" Clinical and Investigative Medicine-Medecine Clinique et experimentale, (1988) vol. 11, No. 6, pp. 441-445., XP009017116.

Black, P. et al.: "A randomized, double-blind, placebo-controlled comparison of the analgesic efficacy, onset of action, and tolerability of ibuprofen arginate and ibuprofen in postoperative dental pain" Clinical Therapeutics, vol. 24, No. 7, 2002, pp. 1072-1089, XP002254117.

Grebe, W. et al.: "A multicenter, randomized, double-blind, double-dummy, placebo-and active-controlled, parallel-group comparison of diclofenac-K and ibuprofen for the treatment of adults with infuenza-like symptoms" Clinical Therapeutics, vol. 25, No. 2, Feb. 3003 (Feb. 2003), pp. 444-458, XP001155030.

Mehlisch, D.R.: "Double-blind crossover comparison of ketoprofen, naproxen, and placebo patients with primary dysmenorrhea" Clinical Therapeutics, vol. 12, No. 5, 1990, pp. 389-409, XP009017199.

Mehlisch, D.R.: "Ketoprofen, ibuprofen, and placebo in the treatment of primary dysmenorrheal: a double-blind crossover comparison" J Clin Pharmacol., , vol. 29, No. 12, Dec. 1988 (Dec. 1988), pp. s29-33, XP009017179.

Palmisano, G.P. et al.: "Double-blind crossover comparison of ketoprofen, ibuprofen, and placebo in the treatment of patients with primary dysmenorrhea" Advances in Therapy, vol. 5, No. 4, 1988, pp. 128-137, XP009017375.

PCT Search Report for PCT/US2003/08846 dated Jun. 10, 2003.
PCT Search Report for PCT/US2004/034709 dated Jun. 29, 2005.
PCT Search Report for PCT/US2004/034708 dated Jan. 26, 2006.

* cited by examiner

NON-STEROIDAL ANTI-INFLAMMATORY DRUG DOSING REGIMEN

CROSS REFERENCE TO RELATED APPLICATIONS

This application is a division of U.S. patent application Ser. No. 10/393,755 filed Mar. 21, 2003, now abandoned, which is incorporated by reference herein in its entirety.

The present invention relates to a novel dosing regimen for non-steroidal anti-inflammatory drugs, particularly propionic acids. This dosing regimen provides sustained therapeutic effect over extended time periods.

BACKGROUND OF THE INVENTION

Therapeutic agents for treating pain, inflammation, and fever include analgesics, anti-inflammatories, and antipyretics. Non-steroidal anti-inflammatory drugs (NSAID's) are one type of such therapeutic agents. They include propionic acid derivatives, acetic acid derivatives, fenamic acid derivatives, biphenylcarbodylic acid derivatives, oxicams, and cyclooxygenase-2 (COX-2) selective NSAID's.

Propionic acids include for example ibuprofen, naproxen, and ketoprofen. Ibuprofen in particular is a widely used, well known NSAID possessing analgesic and antipyrretic properties. It has been commercially available as an over-the-counter drug in many forms for several years. Ibuprofen is chemically known as 2-(4-isobutylphenyl)-propionic acid.

NSAID's are typically administered on a once to four times daily basis, with the daily dose ranging from about 50 to about 2000 milligrams, preferably from about 100 to 1600 and most preferably from about 200 to about 1200 milligrams.

Acetaminophen is a well known analgesic, with a daily dose ranging from about 325 to about 4000 milligrams, preferably from about 650 to about 4000 milligrams. Acetaminophen was first used in medicine by Van Mering in 1893, but only since 1949 has it gained in popularity as an effective alternative to aspirin for analgesic uses in the over the counter market. The pharmacology of APAP is reviewed by B. Ameer et al., Ann. Int. Med. 87, 202 (1977). Considering the widespread use of APAP and the volume of its manufacture, both its manufacture and its use as an analgesic are well known to persons skilled in the art.

It is known to administer NSAID's, acetaminophen, and other drugs in multiple doses over 12 or 24 hours. For example, it is known to administer multiple doses containing equal amounts of ibuprofen over 12 to 24 hours. Sustained release dosage forms containing ibuprofen are also known.

Palmisano et al., *Advances in Therapy*, Vol. 5, No. 4, July/August 1988 reports on a study of ketoprofen and ibuprofen for treating primary dysmenorrhea. This reference discloses the use of multiple doses of ketoprofen (initial dose of 150 mg followed by subsequent doses of 75 mg) and ibuprofen (initial dose of 800 mg followed by subsequent doses of 400 mg).

It is useful to minimize the "drug exposure" of a patient. In other words, to administer the least total amount of drug that will provide the optimal beneficial therapeutic effect. In particular, it is useful to administer analgesics such as NSAIDs or acetaminophen in a regimin which provides maximal relief at minimal total dose per day of drug.

Applicants have now discovered that NSAID's or acetaminophen provided to a mammal, preferably a human, in a specific, two step dosing regimen provide improved therapeutic effect, especially pain relief, compared with known dosing regimens. In particular, an NSAID or acetaminophen is provided to the mammal, either in one dosage form or two dosage forms taken separately, in an initial dose followed by a second dose of about 3 to 5 hours later. No further NSAID or acetaminophen need be provided, yet surprisingly the therapeutic effect of the NSAID acetaminophen lasts at least about 6 hours after administration of the second dose.

SUMMARY OF THE INVENTION

The invention provides a method of administering an NSAID, which consists of providing to a mammal an initial dose of said NSAID followed by a second dose of said NSAID about 3 to 5 hours after administration of said initial dose, said NSAID having a duration of therapeutic effect which lasts at least about 6 hours after administration of said second dose.

The invention also provides a method of administering an NSAID, which comprises providing to a mammal an initial dose of said NSAID followed by a second dose of said NSAID about 3 to 5 hours after administration of said initial dose, with no further provision of NSAID for at least about 6 hours after administration of said second dose, said NSAID having a duration of therapeutic effect which lasts at least about 6 hours after administration of said second dose.

The invention also provides a method of administering a propionic acid derivative to a mammal, over a 12-hour time period, which comprises providing a first peak plasma concentration of said propionic acid derivative of about 25 to about 30 mcg/mL in said mammal about 30 to about 120 minutes after said, initial dose, and a second peak plasma concentration of said propionic acid derivative of about 15 to about 30 mcg/mL about 4.5 to about 5.5 hours after administration of said initial dose.

The invention also provides a method of administering a propionic acid derivative, which comprises providing to a mammal, over a 12 hour time period, an initial dose of said propionic acid derivative at the beginning of said 12 hour time period, followed by a second dose of said propionic acid derivative about 3 to 5 hours after administration of said initial dose, said initial dose being at least about twice said second dose, wherein no further propionic acid derivative is provided during said 12 hour time period.

The invention further provides a dosage form comprising an immediate release portion containing an initial dose of an NSAID and a delayed burst release portion containing a second dose of said NSAID, said initial dose being at least about twice said second dose.

The invention also provides a method of administering acetaminophen, which consists of providing to a mammal an initial dose of acetaminophen followed by a second dose of acetaminophen about 3 to 5 hours after administration of said initial dose, said acetaminophen having a duration of therapeutic effect which lasts at least about 6 hours after administration of said second dose.

The invention also provides a method of administering acetaminophen, which comprises providing to a mammal, over a 12 hour time period, an initial dose of acetaminophen at the beginning of said 12 hour time period, followed by a second dose of acetaminophen about 3 to 5 hours after administration of said initial dose, said initial dose being at least about twice said second dose, wherein no further acetaminophen is provided during said 12 hour time period.

The invention further provides a dosage form comprising an immediate release portion containing an initial dose of acetaminophen and a delayed burst release portion containing a second dose of acetaminophen, said initial dose being at least about twice said second dose.

The invention also provides a method of administering a therapeutic agent, which consists of providing to a mammal an initial dose of a non-steroidal anti-inflammatory drug followed by a second dose of acetaminophen about 3 to 5 hours after administration of said initial dose of non-steroidal anti-inflammatory drug; said non-steroidal anti-inflammatory drug and acetaminophen having a combined duration of therapeutic analgesic effect which lasts at least about 6 hours after administration of said second dose of acetaminophen.

DETAILED DESCRIPTION OF THE INVENTION

Figure 1:
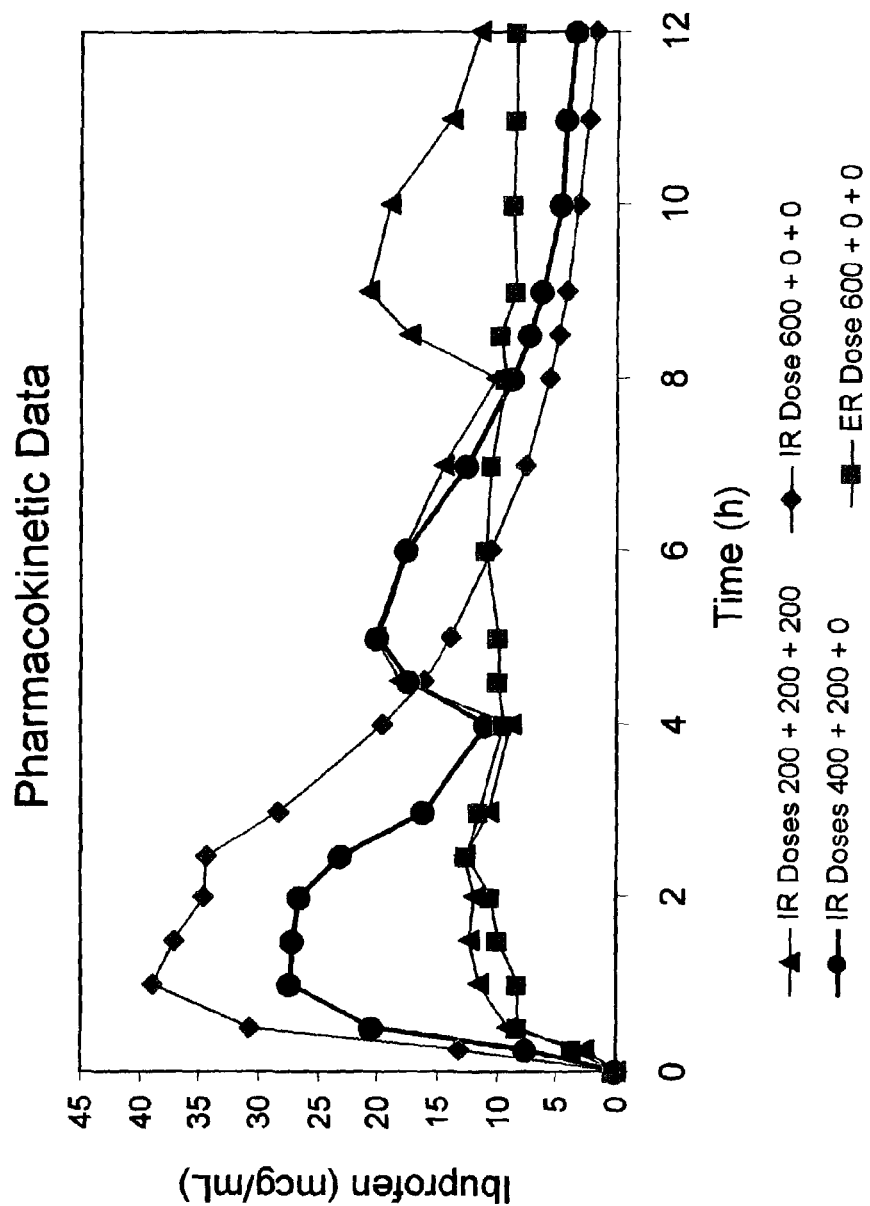
FIG. 1 depicts ibuprofen absorption levels as a function of time for the various dosing regimens reported in Example 1.

As used herein, "ATDAIRD" shall mean the average therapeutic duration of action of an effective immediate release dose" of a particular active ingredient. For example, the typical duration of action of an immediate release dose of ibuprofen or ketoprofen is about 4 to about 6 hours. Accordingly, the ATDAIRD for ibuprofen or ketoprofen is 5 hours. The typical duration of action of an immediate release dose of Naproxen is about 8 to about 12 hours. The ATDAIRD for naproxen, therefore is 10 hours. The therapeutic duration of action of a particular active ingredient can readily be determined from the dosing instructions in the labeling for immediate release products containing that particular active ingredient.

NSAID's useful in the present invention include for example 1) propionic acid derivative NSAID's, 2) acetic acid derivative NSAID's, 3) fenamic acid derivative NSAID's, 4) biphenylcarbodylic acid derivative NSAID's, 5) oxicam NSAID's, 6) cyclooxygenase-2 (COX-2) selective NSAID's, and 7) pharmaceutically acceptable salts of the foregoing.

Examples of acetic acid derivatives are indomethacin, diclofenac, sulindac, tolmetin, and the like. Examples of fenamic acid derivatives are mefanamic acid, meclofenamic acid, flufenamic acid, and the like. Examples of biphenylcarbodylic acid derivatives are diflunisal, flufenisal, and the like. Examples of oxicams are piroxicam, sudoxicam, isoxicam, meloxicam, and the like.

In a particularly preferred embodiment, the NSAID is selected from propionic acid derivatives. Propionic acid derivatives are pharmaceutically acceptable analgesics/non-steroidal anti-inflammatory drugs having a free —CH(CH$_3$) COOH or —CH$_2$CH$_2$COOH or a pharmaceutically acceptable salt group, such as —CH(CH$_3$)COO—Na+ or CH$_2$CH$_2$COO—Na+, which are typically attached directly or via a carbonyl functionality to a ring system, preferably an aromatic ring system.

Examples of useful propionic acid derivatives include ibuprofen, naproxen, benoxaprofen, naproxen sodium, flurbiprofen, fenoprofen, fenbuprofen, ketoprofen, indoprofen, pirprofen, carpofen, oxaprofen, pranoprofen, microprofen, tioxaprofen, suprofen, alminoprofen, tiaprofenic acid, fluprofen and bucloxic acid.

In one embodiment of the invention, the propionic acid derivative is selected from ibuprofen, ketoprofen, flubiprofen, and pharmaceutically acceptable salts and combinations thereof.

Preferably, the propionic acid derivative is ibuprofen, 2-(4-isobutylphenyl)propionic acid, or a pharmaceutically acceptable salt thereof, such as the arginine, lysine, or histidine salt of ibuprofen. Other pharmaceutically acceptable salts of ibuprofen are described in U.S. Pat. Nos. 4,279,926, 4,873,231, 5,424,075 and 5,510,385, the contents of which are incorporated by reference.

Acetaminophen has the formula N-(4-hydroxyphenyl) acetamide and is sometimes referred to as MAP. The preparation of APAP is disclosed in U.S. Pat. No. 2,998,450.

According to the invention, the NSAID or acetaminophen is provided to a mammal in need of treatment, in particular pain relief treatment, in a specific dosing regimen over an extended time period, preferably over a 12 hour period. At time zero, an initial dose of the NSAID or acetaminophen is provided, i.e. administered, to the mammal. Approximately 1 ATDAIRD later, a second dose of the NSAID or acetaminophen is provided to the mammal. After the second dose, no further NSAID or acetaminophen is administered for the remainder of the time period.

In embodiments in which ibuprofen, ketoprofen, or acetaminophen are employed as the active ingredient, the second dose is provided to the mammal approximately 3 to 5, preferably about 4, hours after administration of the first dose. In these embodiments, no further ibuprofen, ketoprofen, or acetaminophen is administered for the remainder of the 12 hour time period.

The initial dose may be for example in the range of about 0.10 to about 15 mg/kg, and the second dose may be for example in the range of about 0.05 to about 7.5 mg/kg. In one embodiment, the initial dose of NSAID or acetaminophen is at least about twice the second dose of NSAID. In certain embodiments of the invention wherein ibuprofen is employed, the initial dose is from about 400 to about 800 mg, or from about 5 to about 12 mg/kg, and the second dose is from about 200 to about 400 mg, or from about 2.9 to about 6.0 mg/kg. In one particular embodiment of the invention wherein ibuprofen is employed, the initial dose is about 400 mg, or about 5.7 mg/kg, and the second dose is about 200 mg, or about 2.9 mg/kg. In certain other embodiments wherein ketoprofen is employed, the initial dose is from about 50 to about 100 mg, or from about 0.70 to about 1.43 mg/kg, and the second dose is from about 25 to about 50 mg, or from about 0.35 to about 0.72 mg/kg. In certain other embodiments wherein acetaminophen is employed, the initial dose is from about 650 to about 1000 mg, or from about 9.2 to about 14.3 mg/kg, and the second dose is from about 325 to about 500 mg, or from about 4.5 to about 7.2 mg/kg. Moreover, the initial dose is within the therapeutic range for the particular active ingredient employed, and is about twice the level of the second dose, which is also within the therapeutic range for the particular active ingredient employed.

The duration of the therapeutic effect of the NSAID or acetaminophen is maintained over the extended time period. In particular, the duration of therapeutic effect of the NSAID or acetaminophen lasts at least about 1.2 times the ATDAIRD for the NSAID after administration of the second dose. In particular embodiments in which the NSAID or acetaminophen has an ATDAIRD of 5 hours, e.g. embodiments in which the active ingredient is selected from ibuprofen, or ketoprofen, or acetaminophen, the duration of therapeutic effect lasts at least about 6 hours after administration of the second dose. It has been discovered that excellent pain relief in particular is maintained over extended time periods, preferably about 12 hours.

In a preferred embodiment of the invention, a propionic acid derivative is administered to a mammal over a 12 hour time period, by first providing to the mammal an initial dose of the propionic acid derivative at the beginning of the 12 hour time period, followed by a second dose of the propionic acid derivative about 3 to 5 hours later, wherein the initial dose is at least about twice the second dose. No further propionic acid derivative is provided during the 12 hour time period.

In another embodiment of the invention, acetaminophen is administered to a mammal over a 12 hour time period, by first providing to the mammal an initial dose of the acetaminophen at the beginning of the 12 hour time period, followed by a second dose of acetaminophen about 3 to 5 hours later, wherein the initial dose is at least about twice the second dose. No further acetaminophen is provided during the 12 hour time period.

In certain embodiments, the invention provides a first peak plasma concentration within the therapeutic range for the particular active ingredient employed within about 0.5 times the ATDAIRD for the active ingredient after administration of the initial dose, and a second peak plasma concentration within the therapeutic range for the particular active ingredient employed between about 0.8 to about 1.2 times the ATDAIRD after administration of the initial dose. In one embodiment, the plasma concentration of NSAID or acetaminophen at about 2 times the ATAIRD after administration of the initial dose is below the known therapeutic range for the particular active ingredient employed.

In certain particular embodiments, in which the active ingredient has an ATDAIRD of about 5 hours, the invention provides a first peak plasma concentration within the therapeutic range for the particular active ingredient employed about 30 to about 120 minutes after administration of the initial dose, and a second peak plasma concentration within the therapeutic range for the particular active ingredient employed between about 4 to about 6.5 hours after administration of the initial dose. In one embodiment, the plasma concentration of NSAID or acetaminophen at about 10 hours after administration of the initial dose is below the known therapeutic range for the particular active ingredient employed.

In certain particular embodiments wherein ibuprofen is employed, the invention provides a first peak plasma concentration of ibuprofen of about 25 to about 30 mcg/mL in the mammal about 30 to about 120 minutes after administration of the initial dose, and a second peak plasma concentration of ibuprofen of about 15 to about 30 mcg/mL about 4.5 to about 5.5 hours after administration of the initial dose. In one embodiment, the plasma concentration of ibuprofen at about 10 hours after administration of the initial dose is less than about 10 mcg/mL. In another embodiment, the plasma concentration of ibuprofen at about 6 hours after the second dose is less than about 10 mcg/mL.

The NSAID or acetaminophen may be administered in a variety of dosage forms, for example, solid dosage forms such as tablets, capsules, liquid dosage forms such as syrups, and suspensions. The NSAID or acetaminophen may also be administered transdermally, or parenterally, such as intravenously, intramuscularly, or subcutaneously. The NSAID or acetaminophen may also be administered rectally, for example as a suppository.

The initial and second doses may be administered together or separately. For example, if administered separately, the initial dose may be administered in a first immediate release dosage form, and the second dose may be administered about 3 to 5 hours later in a second immediate release dosage form.

In one embodiment the initial and second doses are administered in a single dosage form, preferably a single solid dosage form. For example, such a dosage form may comprise a single dosage form comprising an immediate release portion containing the initial dose of NSAID or acetaminophen and a delayed burst release portion containing the second dose of NSAID or acetaminophen. Such a single solid dosage form may be a multilayer tablet, a multiparticulate tablet, or the like. It may optionally include a barrier layer in between the two portions, for example a polymeric barrier.

As used herein, a "burst release profile" refers to a release profile which meets immediate release criteria during a specified interval. The specified interval may optionally follow a predetermined lag time. By "delayed burst release profile" it is meant that the release of at least a portion, or dose, of that particular active ingredient from the dosage form is delayed for a pre-determined time after contact with a liquid medium, such as after ingestion by the patient, and the delay period ("lag time") is followed by prompt (i.e. immediate) release of that dose of active ingredient.

In embodiments wherein the initial and second doses are provided by a dosage form that provides a delayed burst profile, the dissolution of the burst release portion of active ingredient, after the delay period, meets USP specifications for immediate release tablets containing that active ingredient. For example, for acetaminophen tablets, USP 24 specifies that in pH 5.8 phosphate buffer, using USP apparatus 2 (paddles) at 50 rpm, at least 80% of the acetaminophen contained in the dosage form is released therefrom within 30 minutes after dosing, and for ibuprofen tablets, USP 24 specifies that in pH 7.2 phosphate buffer, using USP apparatus 2 (paddles) at 50 rpm, at least 80% of the ibuprofen contained in the dosage form is released therefrom within 60 minutes after dosing. (See USP 24, 2000 Version, 19-20 and 856 (1999)).

The following examples further illustrate the invention, but are not meant to limit the invention in any way.

Example 1

A double-blind, randomized, parallel, placebo-controlled, single center, PK/PD dental pain study was conducted over a 12 hour observation period to evaluate the pharmacokinetic, pharmacodynamic, efficacy and safety profiles of certain ibuprofen dosing regimens. Specifically, a single dose of 600 mg ibuprofen extended release caplets was compared with equivalent total doses of ibuprofen immediate release 200 mg caplets administered in three different dosing regimens as well as placebo in the treatment of moderate to severe post-operative dental pain.

The ibuprofen was administered as ibuprofen extended release 600 mg caplets or one or more ibuprofen immediate release 200 mg caplets.

The patients evaluated in this study consisted of male or non-pregnant and non-lactating female out-patient volunteers, 16 years of age or older, complaining of moderate to severe pain following the surgical extraction of three or four third molars with at least one partial or complete bony impacted third mandibular molar. The term impacted included: partial bony impaction, bony impaction, or complicated bony impaction. A total of 210 patients were entered into the study. 208 patients were eligible for the efficacy analyses.

All patients who met the entrance criteria were enrolled in one of two study sub-groups. One sub-group of patients had both pharmacokinetic and pharmacodynamic evaluation (PK group). The other sub-group of patients had only the analgesic efficacy evaluations (non-PK group). A separate randomization schedule was used for each of the two sub-groups. Patients from both subgroups were assigned at random to one of the five following treatments:

| Ibuprofen Extended Release | 600 mg single dose at 0 hour |
| Ibuprofen Immediate Release | 600 mg single dose at 0 hour |
| Ibuprofen Immediate Release | 400 mg at 0 hour; 200 mg at 4 hours |
| Ibuprofen Immediate Release | 200 mg at 0, 4, and 8 hours |
| Placebo | |

Patients' assessments of pain intensity and pain relief as well as blood samples for plasma ibuprofen analysis were obtained at the study site at hours 0, 0.25, 0.5, 1, 1.5, 2, 2.5, 3, 4, 4.5, 5, 6, 7, 8, 8.5, 9, 10, 11 and 12. A stopwatch technique was used to measure the onset of meaningful pain relief.

Figure 2:
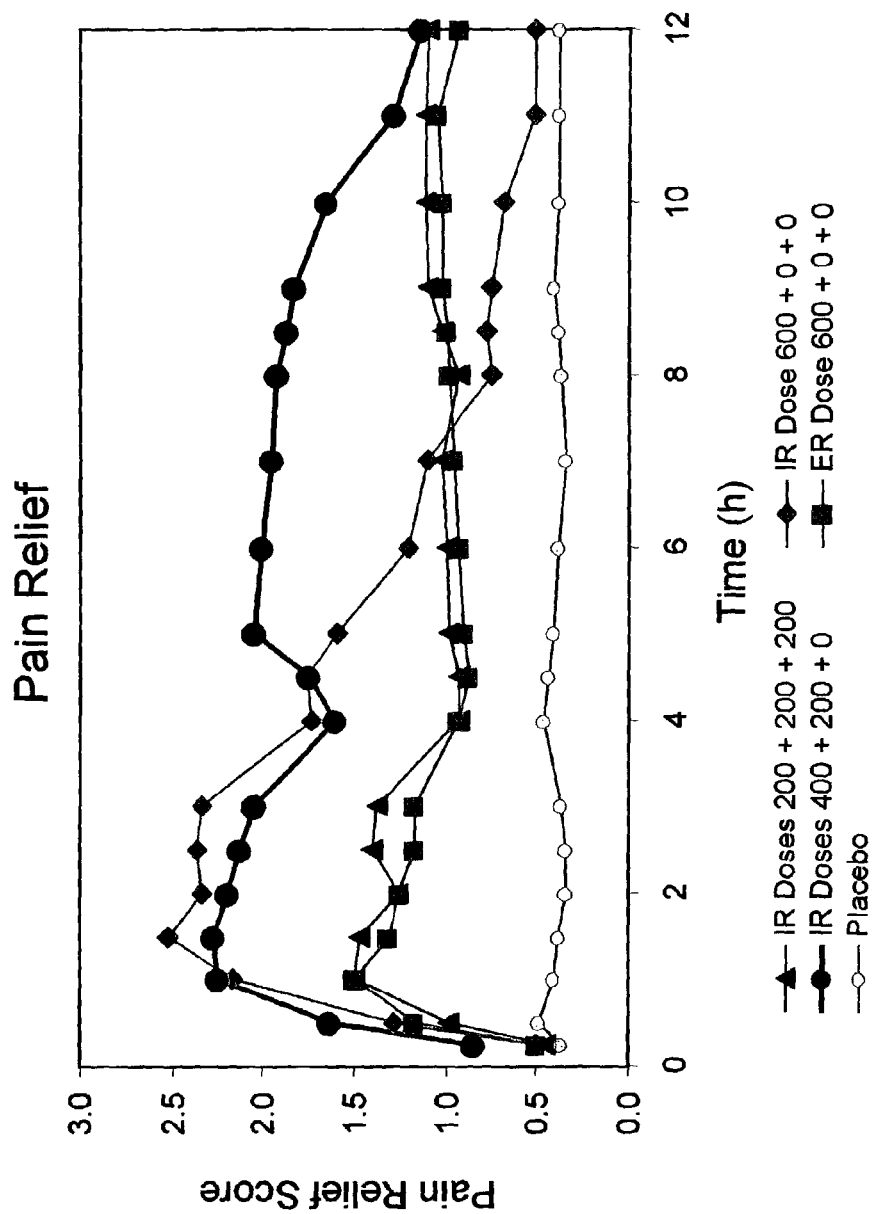
FIG. 2 depicts the pain relief scores as a function of time for the dosing regimens reported in Example 1.

FIG. 1 shows the blood levels of ibuprofen achieved with the four non-placebo treatments as a function of time over the 12 hour study period. FIG. 2 depicts the pain relief scores as a function of time for the five treatments including placebo. Surprisingly, the 400/200/0 administration of ibuprofen according to the invention provided excellent pain relief over the entire 12 hour study period. During the first four hours, the 400/200/0 treatment, along with the 600/0/0 immediate release treatment, provided superior pain relief over the other treatments. During the 4 to 12 hour interval, the 400/200/0 treatment alone provided the highest pain relief scores, despite the fact that no further ibuprofen was administered after the first four hours.

Figure 3:
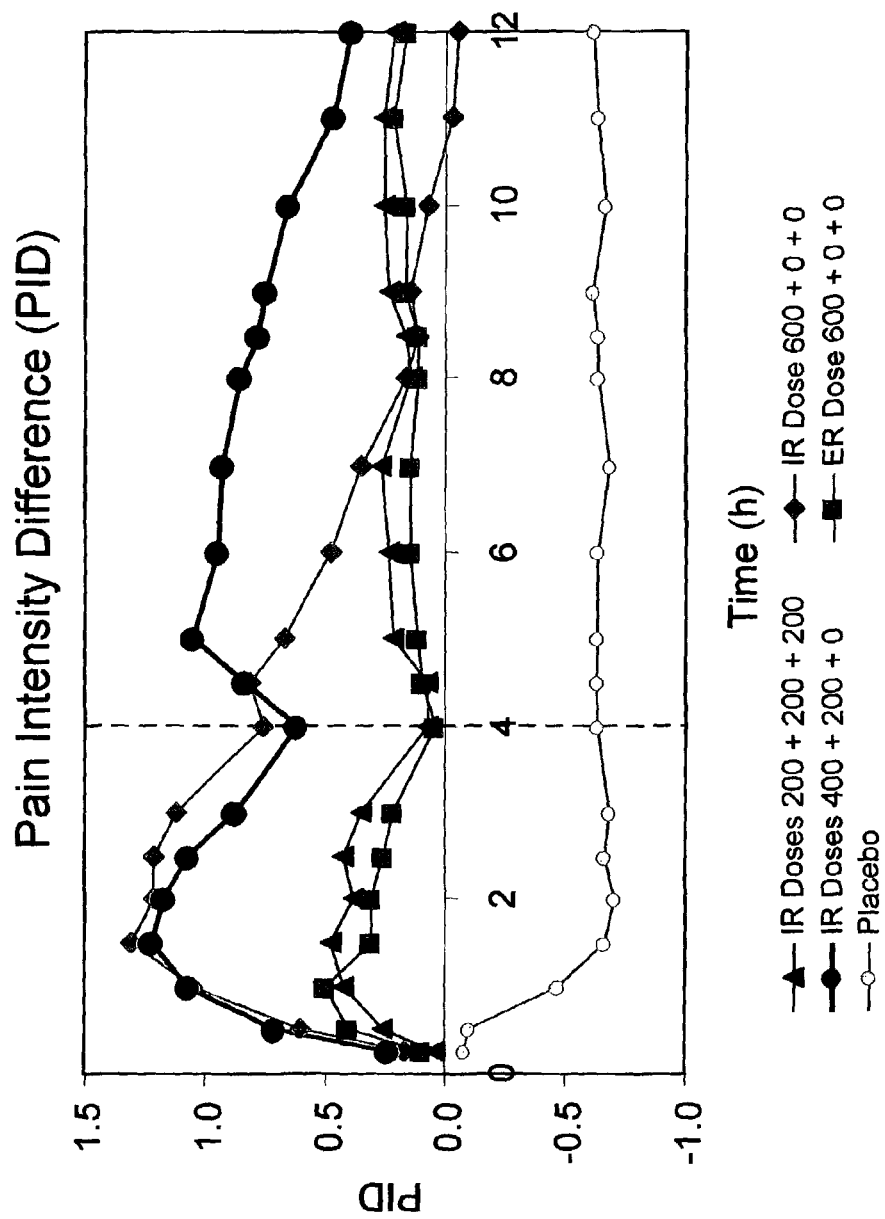
FIG. 3 depicts the pain intensity differences (ND) as a function of time for the dosing regimens reported in Example 1.

Similarly, FIG. 3 shows the pain intensity differences (PID) reported as a function of time for all five treatments. Again, the 400/200/0 treatment according to the invention provided the best PID over the 12 hour study period, particularly after the four hour mark, when the PID's reported for other treatments declined. This is surprising in that the treatment according to the invention did not include further administration of ibuprofen after hour four.

Example 2

A dosage form according to the invention is made as follows. The dosage form is an immediate release/delayed burst release combination capsule containing 200 mg and 100 mg of ibuprofen, respectively. The immediate release portion is in the form of granules, while the delayed burst release portion is in the form of a compression-coated core.

Step A

First, an ibuprofen granulation is prepared from the following ingredients:

| Ingredient | Trade Name | Manufacturer | Mg/Tablet |
| --- | --- | --- | --- |
| Ibuprofen powder | | Albemarle Corp. Orangeburg, SC | 100 |
| Microcrystalline cellulose | Avicel pH 101 | FMC Corp. Newark, DE 19711 | 5.4 |
| Pregelatinized starch | National 1551 | National Starch & Chem. Co. Bridgewater, NJ | 2.2 |
| Magnesium stearate | | Mallinckrodt Inc., St. Louis, Missouri | 1.1 |
| Total | | | 108.7 |

The ibuprofen powder, AVICEL pH 101 and pregelatinized starch are mixed in a (5 qt) bowl of a planetary mixer (Hobart Corp., Dayton, Ohio). Water is added to the powder mixture while mixing at low speed. Mixing is continued for 10 minutes. The granulation is removed from the bowl and dried at room temperature for 12 to 16 hours to remove all residual solvent. The granules are screened through a #20 mesh screen and placed in a (2 qt) P-K blender. Magnesium stearate is added to the dry granules, followed by mixing for 5 more minutes.

Step B

The granulation of Step A is compressed into cores on a Beta Press (Manesty, Liverpool, UK). The press is equipped with 6 mm diameter round, concave punch and die units. The granulation is fed into the die cavity of the press and pressed into solid cores using 1500 lb/sq. in. of operating pressure. The compressed cores weigh 109 mg and contained 100 mg of ibuprofen.

Step C

An ethylcellulose powder is prepared as a compression-coating for the sustained burst release portion of the dosage form. The following ingredients are used:

| Ingredient | Manufacturer | Mg/Tablet |
| --- | --- | --- |
| Ethylcellulose powder (grade N-10-F) | Shin-Etsu Chem. Ind. Co. Ltd. Tokyo, Japan | 304.6 |
| Magnesium stearate | Mallinckrodt Inc., St. Louis, Missouri | 1.4 |
| Total | | 306 |

The ethylcellulose powder and magnesium stearate are placed in a (2-quart) P-K blender and mixed for 5 minutes.

Step D

Compression-coated cores are prepared by using a model M hydraulic Carver Laboratory Press (Fred S. Carver, Inc., Hydraulic Equipment, Summit, N.J.). The press is equipped with 9 mm round, concave punch and die units. Each core is prepared by first filling 153 mg of the ethylcellulose powder from Step C into a die, and then manually placing a core from Step B in the center of the powder. The remaining 153 mg of ethylcellulose powder is then poured into the die, which is then compressed at 3000 lb/square inch of operating pressure to prepare the compression-coated core. The compression-coated cores weigh 415 mg and contain 100 mg of ibuprofen.

Step E

The finished dosage form comprising immediate release and delayed burst release portions of ibuprofen is made as follows. 218 mg of the ibuprofen granulation from Step A is filled into the first half of a capsule (DB Caps, size AA, Capsugel, Morris Plains, N.J.). Next, a compression-coated core of Step D is manually placed into the capsule. The second half of the capsule is then inserted into the first half of the capsule. The finished dosage form contains 218 mg of ibuprofen granulation (equivalent to 200 mg of ibuprofen) as the immediate release portion of ibuprofen and a 415 mg compression-coated ibuprofen core (equivalent to 100 mg of ibuprofen) as the delayed burst release dose of the ibuprofen.

Example 3

A dosage form according to the invention is made as follows. The dosage form is an immediate release/delayed burst release combination capsule containing 200 mg and 100 mg of ibuprofen, respectively. The immediate release portion is in the form of granules, while the delayed burst release portion is in the form of a spray-coated core.

Step A
An ibuprofen granulation for the immediate release portion is prepared as in Example 2 above.

Step B
The granulation of Step A is compressed into cores as in Example 2 above.

Step C
A coating dispersion for the sustained burst release portion of the dosage form is prepared using the following ingredients:

| Coating | Trade Name | Manufacturer | Mg/Tablet |
|---|---|---|---|
| Hydroxypropyl methylcellulose | Methocel K4M | The Dow Chemical Company, Midland, Michigan 48674 | 20.8 |
| Talc | | Charles B. Chrystal Co. New York, NY | 8.3 |
| Povidone | Kollidon K-30 | BASF Corp. Parsipany, NJ | 10.4 |
| Polyethylene Glycol 400 | | Union Carbide Corporation, Danbury, CT 06817 | 4.1 |
| Ethanol (dried as solvent) | | | |
| Water (dried as solvent) | | | |
| Total | | | 43.6 |

The coating dispersion is prepared by adding the hydroxypropyl methylcellulose, talc, povidone, and polyethylene glycol 400 to a suitable ethanol/water mixture (94%/4%) to produce a 10.5% polymeric dispersion. The dispersion is allowed to sit at room temperature for 12 hours.

Step D
Spray-coated ibuprofen cores are prepared as follows. The cores of Step B are placed in a 24" Acella Coating pan (Manesty, Liverpool, UK) and air tumbled with the coating dispersion of Step C until the cores are uniformly coated. The coated cores are dried in an oven at 50° C. for 24 hours to evaporate the solvent. The coated cores weigh 153 mg and contain 100 mg of ibuprofen.

Step E
The finished dosage form comprising immediate release and delayed burst release portions of ibuprofen is made as follows. 218 mg of the ibuprofen granulation of Step A is filled into a first half of a capsule (DB Caps, size AA, Capsugel, Morris Plains, N.J.). A spray-coated ibuprofen core of Step D is manually placed into the capsule. The second half of the capsule is then inserted into the first half to yield the finished dosage form. The finished dosage form contains 218 mg of ibuprofen granulation (equivalent to 200 mg of ibuprofen) as the immediate release portion of the ibuprofen and a 153 mg spray-coated ibuprofen core (equivalent to 100 mg of ibuprofen) as the delayed burst release portion of ibuprofen.

We claim:

1. A method of administering a non-steroidal anti-inflammatory drug, which consists of providing to a mammal a dosage form comprising an initial dose of an immediate release portion containing said non-steroidal anti-inflammatory drug and a second dose of a delayed burst release portion containing said non-steroidal anti-inflammatory drug that is released about 4 hours after administration of said initial dose, said non-steroidal anti-inflammatory drug having a duration of therapeutic effect which lasts at least about 6 hours after administration of said second dose, wherein said initial dose is at least about twice said second dose.

2. The method of claim 1, wherein said initial dose is about 5 mg/kg to about 12 mg/kg and said second dose is about 2.9 mg/kg to about 6 mg/kg.

3. The method of claim 1, wherein said non-steroidal anti-inflammatory drug is a propionic acid derivative.

4. The method of claim 3, wherein said propionic acid derivative is selected from the group consisting of ibuprofen, naproxen, benoxaprofen, naproxen sodium, flurbiprofen, fenoprofen, fenbuprofen, ketoprofen, indoprofen, pirprofen, carpofen, oxaprofen, pranoprofen, microprofen, tioxaprofen, suprofen, alminoprofen, tiaprofenic acid, fluprofen and bucloxic acid.

5. The method of claim 4, wherein said propionic acid derivative is ibuprofen.

6. The method of claim 1, wherein said initial dose and said second dose are administered to the mammal in separate dosage forms.

7. The method of claim 1, wherein said dosage form is a solid dosage form.

8. The method of claim 1, wherein said therapeutic effect is pain relief.

9. A method of administering a propionic acid derivative to a mammal, over a 12-hour time period, which comprises providing a dosage form comprising an initial dose of an immediate release portion and a second dose of a delayed burst release portion of said propionic acid derivative to said mammal, wherein said dosage form provides a first peak plasma concentration of said propionic acid derivative of about 25 to about 30 mcg/mL in said mammal about 30 to about 120 minutes after said initial dose, and a second peak plasma concentration of said propionic acid derivative of about 15 to about 30 mcg/mL about 45 to about 5.5 hours after administration of said initial dose.

10. The method of claim 9, wherein the plasma concentration in said mammal at about 10 hours after administration of the initial dose is less than about 10 mcg/mL.

11. A method of administering a propionic acid derivative, which comprises providing to a mammal, over a 12 hour time period, a dosage form comprising an initial dose of an immediate release portion and a second dose of a delayed burst release portion of said propionic acid derivative, wherein said initial dose of said propionic acid derivative is released at the beginning of said 12 hour time period, followed by said second dose of said propionic acid derivative about 4 hours after administration of said initial dose, wherein said initial dose is at least about twice said second dose and no further propionic acid derivative is provided during said 12 hour time period.

12. The method of claim 11, wherein said propionic acid derivative is ibuprofen.

13. The method of claim 11, wherein said initial dose is about 400 nag and said second dose is about 200 mg.

14. A method of administering acetaminophen, which consists of providing to a mammal a dosage form comprising an initial dose of an immediate release portion and a second dose of a delayed burst release portion of said acetaminophen, wherein said initial dose of acetaminophen is followed by said second dose of acetaminophen about 4 hours after administration of said initial dose, said acetaminophen having a duration of therapeutic effect which lasts at least about 6 hours after administration of said second dose.

15. The method of claim 14, wherein said second dose is at least about twice said first dose.

16. The method of claim 14, wherein said second dose is administered about 4 hours after said initial dose.

17. The method of claim 14, wherein said initial dose and said second dose are administered to the mammal in separate dosage forms.

18. The method of claim 14, wherein said dosage form is a solid dosage form.

19. The method of claim 14, wherein said therapeutic effect is pain relief.

20. A method of administering acetaminophen, which comprises providing to a mammal, over a 12 hour time period, a dosage form comprising an initial dose of an immediate release portion and a second dose of a delayed burst release portion of said acetaminophen, wherein said initial dose of acetaminophen at the beginning of said 12 hour time period, is followed by said second dose of acetaminophen about 4 hours after administration of said initial dose, wherein said initial dose is at least about twice said second dose and no further acetaminophen is provided during said 12 hour time period.

21. A method of reducing drug exposure of a mammal to an NSAID comprising providing said NSAID to said mammal using the method of claim 1.

22. A method of administering a therapeutic agent, which consists of providing to a mammal a dosage form comprising an initial dose of an immediate release portion of a non-steroidal anti-inflammatory drug and a second dose of a delayed burst release portion of acetaminophen, wherein said initial dose of said non-steroidal anti-inflammatory drug is followed by said second dose of acetaminophen about 4 hours after administration of said initial dose of non-steroidal anti-inflammatory drug; said non-steroidal anti-inflammatory drug and acetaminophen having a combined duration of therapeutic analgesic effect which lasts at least about 6 hours after administration of said second dose of acetaminophen.

23. A method of reducing drug exposure of a mammal to an NSAID comprising providing said NSAID to said mammal using the method of claim 9.

* * * * *